(12) United States Patent
Halbert et al.

(10) Patent No.: US 11,241,324 B2
(45) Date of Patent: Feb. 8, 2022

(54) STENT DELIVERY CATHETER WITH FINE THUMBWHEEL CONTROL AND FAST CRANK HANDLE

(71) Applicant: Cardinal Health Switzerland 515 GmbH, Baar (CH)

(72) Inventors: Phillip Halbert, Milpitas, CA (US); Matt Gill, Milpitas, CA (US); Sean Higginson, Milpitas, CA (US)

(73) Assignee: CARDINAL HEALTH SWITZERLAND 515 GMBH, Baar (CH)

( * ) Notice: Subject to any disclaimer, the term of this patent is extended or adjusted under 35 U.S.C. 154(b) by 177 days.

(21) Appl. No.: 16/128,165

(22) Filed: Sep. 11, 2018

(65) Prior Publication Data
US 2019/0076280 A1 Mar. 14, 2019

Related U.S. Application Data

(60) Provisional application No. 62/558,104, filed on Sep. 13, 2017.

(51) Int. Cl.
| | | |
|---|---|---|
| *A61F 2/95* | (2013.01) | |
| *A61F 2/966* | (2013.01) | |
| *A61F 2/97* | (2013.01) | |
| *A61B 17/00* | (2006.01) | |

(52) U.S. Cl.
CPC ............ *A61F 2/9517* (2020.05); *A61F 2/966* (2013.01); *A61F 2/97* (2013.01); *A61B 2017/00389* (2013.01); *A61F 2002/9505* (2013.01)

(58) Field of Classification Search
CPC .. A61F 2/966; A61F 2/95; A61F 2/962; A61F 2/97; A61F 2/9517; A61B 2017/00389; A61B 2017/00393
See application file for complete search history.

(56) References Cited

U.S. PATENT DOCUMENTS

| | | | |
|---|---|---|---|
| 4,580,568 A | 4/1986 | Gianturco | |
| 4,732,152 A | 3/1988 | Wallsten et al. | |
| 6,019,778 A | 2/2000 | Wilson et al. | |
| 7,223,272 B2* | 5/2007 | Francese | A61B 17/1285 606/139 |
| 2005/0060016 A1* | 3/2005 | Wu | A61F 2/95 623/1.11 |

(Continued)

FOREIGN PATENT DOCUMENTS

| | | |
|---|---|---|
| EP | 2111826 A1 | 10/2009 |
| WO | 08/12844 A1 | 10/2008 |

(Continued)

OTHER PUBLICATIONS

International Search Report and Written Opinion for International Application No. PCT/IB2018/01118, dated Jan. 29, 2019.

(Continued)

*Primary Examiner* — Sarah A Simpson
(74) *Attorney, Agent, or Firm* — Arent Fox LLP

(57) ABSTRACT

Various embodiments for a stent delivery device that utilizes a first mode of actuation for slow retraction of an outer sheath and a second mode of actuation for fast retraction of the outer sheath during delivery of a self-expanding implantable device such as a stent or stent graft.

16 Claims, 9 Drawing Sheets

(56) References Cited

U.S. PATENT DOCUMENTS

| | | | |
|---|---|---|---|
| 2005/0267518 A1* | 12/2005 | Wright | ............... A61B 17/1327 |
| | | | 606/203 |
| 2009/0270969 A1 | 10/2009 | Fargahi et al. | |
| 2010/0168756 A1 | 7/2010 | Dorn et al. | |
| 2012/0041537 A1 | 2/2012 | Parker | |
| 2015/2004153 | 2/2012 | Parker et al. | |
| 2012/0059448 A1* | 3/2012 | Parker | ..................... A61F 2/966 |
| | | | 623/1.11 |
| 2016/0074184 A1 | 3/2016 | Cummins et al. | |

FOREIGN PATENT DOCUMENTS

| | | |
|---|---|---|
| WO | 2008124844 A1 | 10/2008 |
| WO | 10/120671 A1 | 10/2010 |
| WO | 12/116368 A2 | 8/2012 |

OTHER PUBLICATIONS

International Preliminary Report on Patentability in International Patent Application No. PCT/IB2018/001118, dated Mar. 17, 2020.

* cited by examiner

STENT DELIVERY CATHETER WITH FINE THUMBWHEEL CONTROL AND FAST CRANK HANDLE

PRIORITY CLAIM AND RELATED APPLICATIONS

This application claims priority under 35 U.S.C. § 119 or the Paris Convention from U.S. Provisional Patent Application 62/558,104 filed Sep. 13, 2017, the entire contents of which is incorporated herein by reference as if set forth in full herein.

BACKGROUND

It is well known to employ various intravascular endo-prostheses delivered percutaneously for the treatment of diseases of various body vessels. These types of endoprosthesis are commonly referred to as "stents". A stent (which includes covered stents or stent-graft) is a generally longitudinal tubular device of biocompatible material, such as stainless steel, cobalt-chromium, nitinol or biodegradable materials, having holes or slots cut therein to define a flexible framework so they can be radially expanded, by a balloon catheter or the like, or alternately self-expanded due to its shape memory characteristic of the material within a biological vessel. The stents are usually configured as a series of hoops with each defined by cylinder-like framework. The framework is usually a series of alternating sequence of struts with a vertex between each pair of struts and configured so that the vertex of one hoop facing a vertex of the adjacent hoops may be connected together. The struts are configured to move and thereby allow the stent to be compressed or "crimped" into a smaller outer diameter so that they can be mounted inside a delivery system.

The delivery systems are used to convey the stent to a desired location for treatment, and then deploy them in position. Many such stents are resiliently compressed to a smaller initial size for containment, protection, storage and eventual delivery from inside a catheter system. Upon deployment, the stents may resiliently self-expand to a larger deployed size.

A successful example of a delivery catheter system, in this case for a self-expanding stent, is described in U.S. Pat. No. 6,019,778 entitled "Delivery Apparatus For A Self-Expanding Stent," to Wilson et al. issued Feb. 1, 2000. The disclosure of this patent is incorporated by reference in the present application, and generally discloses a flexible catheter system shown in a representative diagrammatic form in FIG. 10 of Wilson, including coaxially arranged inner and outer catheter members, each having a hub affixed to its proximal end. The outer sheath is described in the '778 patent as an elongated tubular member having distal and proximal ends, which is made from an outer polymeric layer, an inner polymeric layer, and a braided reinforcing layer between them. The inner shaft is described in the '778 patent as being located coaxially within the outer sheath and has a flexible tapering distal end, which generally extends distally beyond the distal end of the outer sheath. The inner shaft member also is shown as including a stop which is positioned proximal from the distal end of the outer sheath. A self-expanding stent is located within the outer sheath, and is located between the stop on the inner shaft member and the outer sheath distal end. To deploy the stent the outer sheath is withdrawn by a physician in a proximal direction, while the inner shaft member is held in position.

Additional examples of different types of known self-expanding stent delivery systems are shown in U.S. Pat. No. 4,580,568 issued to Gianturco on Apr. 8, 1986; as well as U.S. Pat. No. 4,732,152 issued to Wallsten et al., on Mar. 22, 1988.

In operation, these known stent delivery systems are generally advanced within a body of a patient along a desired vascular path or other body passageway, until the stent within the catheter system is located at a desired site for treatment. While watching the relative positions of the stent and the catheter system components with respect to a stenosis on a video x-ray fluoroscopy screen, the physician holds the proximal hub attached to the inner shaft member in a fixed position with one hand, while simultaneously gently withdrawing the proximal hub attached to the outer tubular sheath with the other hand.

For several reasons, this deployment operation may require some measure of delicate skill. For example, among these reasons is the dynamic blood flow at the desired site for treatment, which may be further disrupted by the presence of a lesion or stenosis to be treated. Another factor is the gradual resilient expansion of a stent as the outer sheath is retracted. This gradual expansion presents an opportunity for a possible reverse "watermelon-seed" phenomenon to occur. This reverse watermelon-seed effect may cause the resilient stent to tend to push the outer sheath back in a proximal direction with a force that tends to change as the sheath is progressively retracted.

As a result, the physician may need to accurately hold the two proximal hubs in a specific relative position, holding them against this expansion force, while attempting to very accurately position the stent up until contact with the anatomy. One of the possibilities that may affect the positioning of the deployed stent is that the inner shaft should preferably be held stationary in the desired position. If the physician's hand that holds the inner shaft hub does inadvertently move during deployment, it is possible that the stent may be deployed in a non-optimum position.

Another possible factor is that the inner and outer catheter shaft members, like any other elongated object, do not have infinite column strength, which may present an opportunity for the position and movement of each proximal hub to differ from the position and movement of the respective distal ends of the inner and outer shaft members. Yet another factor is that the position of the stent may be adjusted up until the point at which a portion of the expanding portion of the stent touches the sidewalls of the body passage, so that the position of the stent should preferably be carefully adjusted until immediately before a portion of the stent touches the anatomy.

Some known catheter systems require two-handed operation, such as those with a pair of independent hubs, one hub on the inner and outer shaft member, respectively. Other known catheter systems include a pistol and trigger grip, with a single mode of deployment, involving a single trigger pull to deploy the associated stent.

SUMMARY OF THE DISCLOSURE

Applicant has devised a stent delivery system that includes a catheter tip, housing, and a wheel. The catheter tip is coupled to an inner shaft and an outer sheath with a stent disposed between the inner shaft and the outer sheath. The inner shaft and the outer sheath extends from a distal end to a proximal end. The catheter tip is coupled to an inner shaft and an outer sheath with a stent disposed between the inner shaft and the outer sheath. The housing extends along a longitudinal axis from a first end to a second end. A sharp member is disposed in the housing and configured to cut the outer sheath along a surface of the outer sheath. A spool hub is mounted in the housing and configured to wind the outer sheath after being cut by the sharp member. A wheel mounted on the housing and coupled to the hub such that rotation of the wheel causes the outer sheath to move along the longitudinal axis relative to the inner shaft toward the second end, wherein the wheel is configured for a first mode of actuation that ergonomically favors translation of the outer shaft at a first rate and for a second mode of actuation that ergonomically favors translation of the outer shaft at a second rate that is greater than the first rate.

A method of delivering a self-expanding stent to selected location in a body vessel can be achieved by: moving a stent to a selected location in a body vessel, the stent being disposed adjacent a catheter tip and confined between an inner shaft and an outer sheath at a distal end of a delivery system; winding the outer sheath so that the outer sheath is moved relative to the inner shaft along a direction from the distal end toward a proximal end of the delivery system at a first rate of change of distance to allow a portion of the self-expanding stent to be expanded into the body vessel; cutting through at least an outer surface of the outer sheath so that the outer sheath is substantially flattened; and rotating the substantially flattened outer sheath using a second mode of actuation that ergonomically favors translation of the outer shaft at a second rate that is greater than the first rate so that the outer sheath is moved relative to the inner shaft along a direction from the distal end toward a proximal end of the delivery system to allow complete deployment of the self-expanding stent in the body vessel.

For each of the embodiments described above, the following features can be utilized in various permutations with each of the embodiments. For example, the wheel has a mounted crank arm so that continuous rotation of the crank arm causes the outer sheath to move along the longitudinal axis relative to the inner shaft toward the second end, wherein the first mode of actuation comprises manipulating the wheel directly and the second mode of actuation comprises manipulating the crank arm; the crank arm is mounted to the wheel with a length of the crank arm being at least equal to the radius of the wheel; the crank am} is mounted on a pivot proximate the circumference of the wheel so that the crank arm can be folded into a slot formed on the surface of the wheel to present a substantially continuous surface; a tubular member is coupled to the outer sheath at a location distal to the sharp member; a hypotube is coupled to the outer sheath at a location distal to the sharp member; a spiral spring is mounted in the housing with one end of the spiral spring connected to the wheel and the other end of the spiral spring is connected to the housing; the spiral spring is disposed in a hub defined by the wheel; the wheel is mounted offset with respect to the longitudinal axis; the wheel is mounted orthogonal with respect to the longitudinal axis; the wheel is mounted flush with respect to a side surface of the housing.

These and other embodiments, features and advantages will become apparent to those skilled in the art when taken with reference to the following more detailed description of the exemplary embodiments of the invention in conjunction with the accompanying drawings that are first briefly described. As well, it is intended that these embodiments, features and advantages may be claimed in this or additional applications for patents.

BRIEF DESCRIPTION OF DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. The term "stent" is intended to encompass an uncovered framework as well as one that is covered by a suitable material (e.g., stent-graft). The term "proximal" is used to denote the location closer to the operator and "distal" is used to denote a location further away from the operator or the health care provider.

Figure 1:
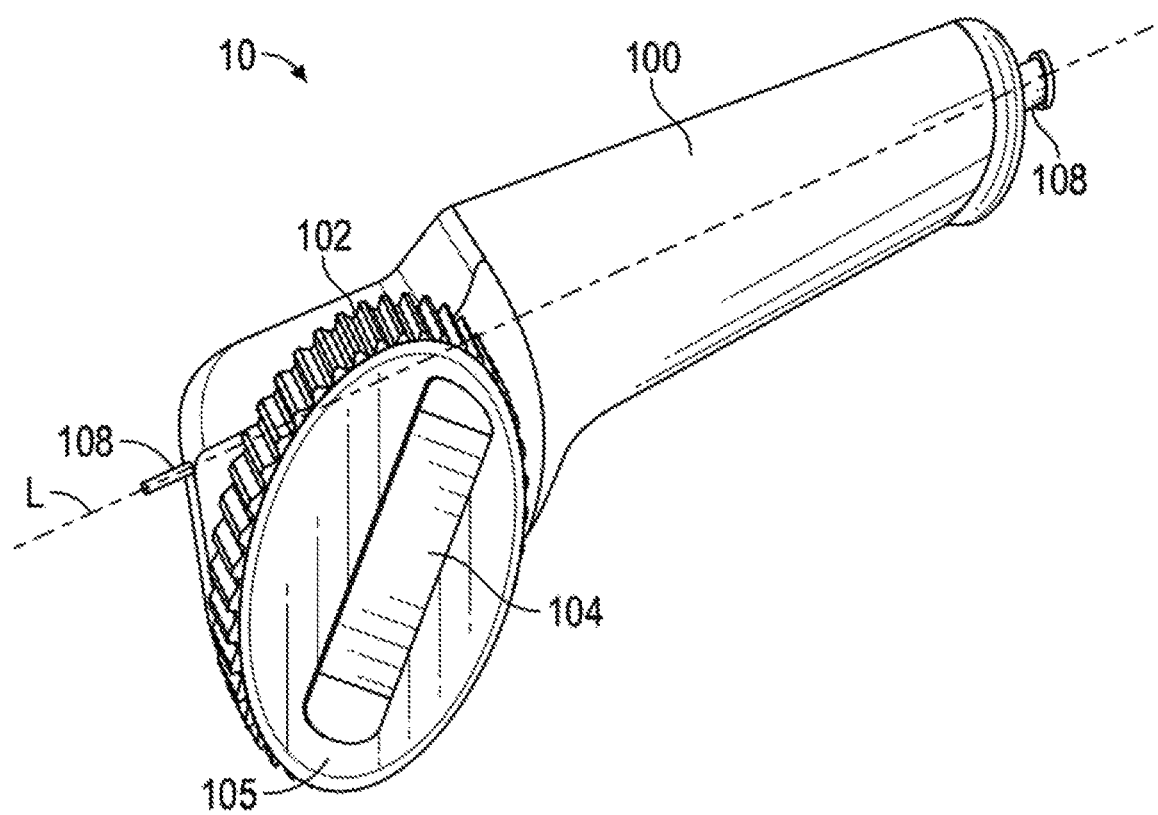
FIG. 1 illustrates a perspective view of a handle according to an embodiment.

Referring now to the figures wherein like numerals indicate the same element throughout the views, there is shown in FIG. 1 a portion of the delivery system 10 in the form of a handle that defines a housing 100. The housing 100 extends along a longitudinal axis L-L from a proximal end to a distal end. A wheel (e. g., thumbwheel) 102 is mounted to the housing 100. An outer sheath 108 is coupled to the wheel 102 to allow for retraction of the sheath 108 at the distal end. As will be described below, it is desirable to deploy a medical device such as a stent by releasing it at varying rates. For example, during initial positioning, the medical device may be released at a first rate and then at a second rate after the initial positioning is acceptable, with the second rate being greater than the first rate. Thus, wheel 102 is configured for a first mode of actuation that ergonomically favors translation of outer shaft 108 at the first rate and for a second mode of actuation that ergonomically favors translation of outer shaft 108 at the second rate. In this embodiment, the first mode of actuation involves manipulating wheel 102 directly. A crank arm 104 is mounted to wheel 102 and is disposed in a slot 105 so that the crank arm can be flipped out. Correspondingly, the second mode of actuation involves manipulating the crank arm 104.

Figure 7A:
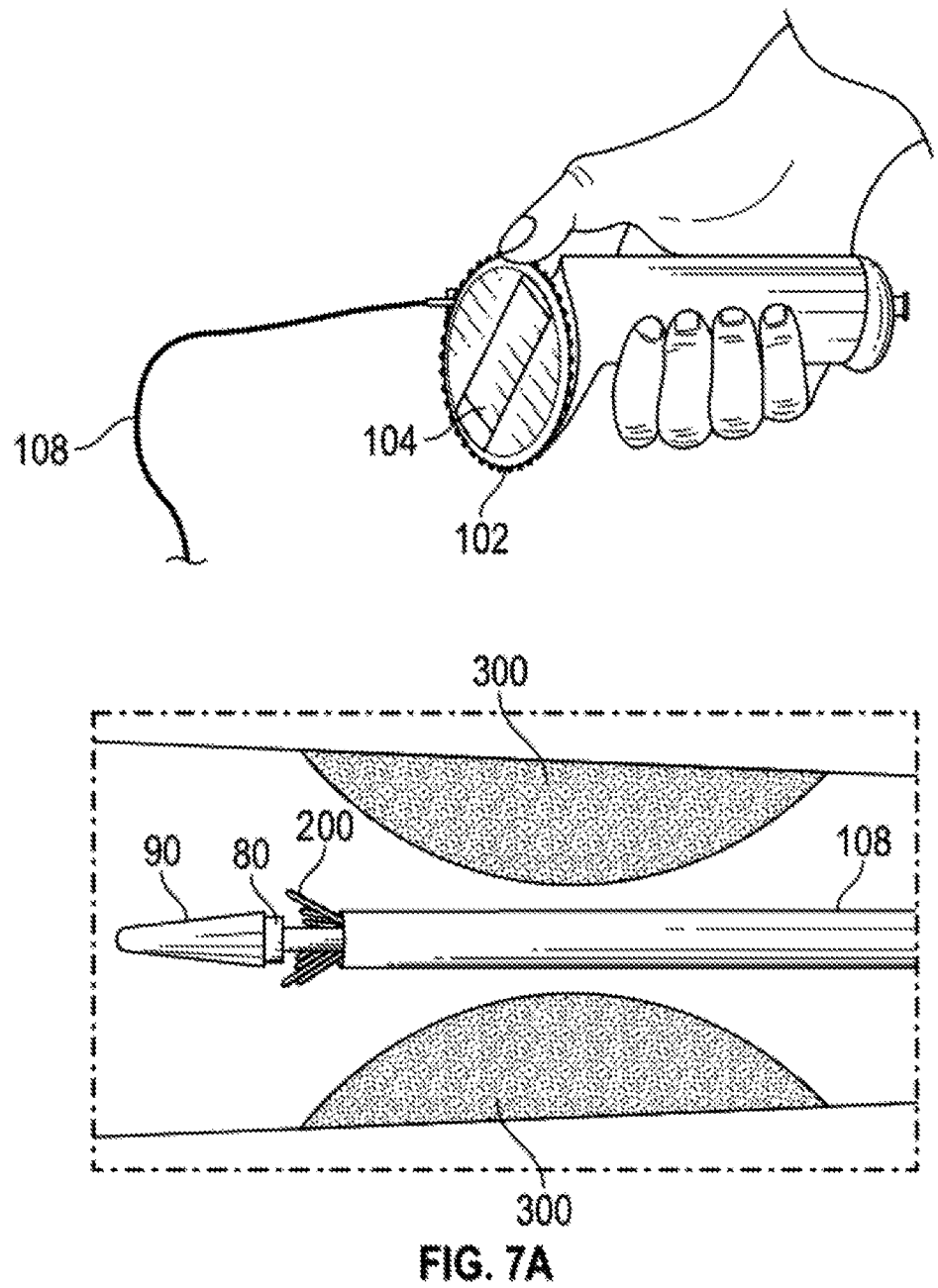
FIGS. 7A and 7B illustrate the operation of the system.

At the distal end of the system 10, a catheter tip 90 (FIG. 7A) is coupled to an inner shaft 80 and outer sheath 108 with a stent 200 disposed or confined between the inner shaft 80 and the outer sheath 108. As can be seen in FIG. 7A, the inner shaft 80 and the outer sheath 108 extends from a distal end, adjacent stent 200, to a proximal end at housing 100.

Figure 4A:
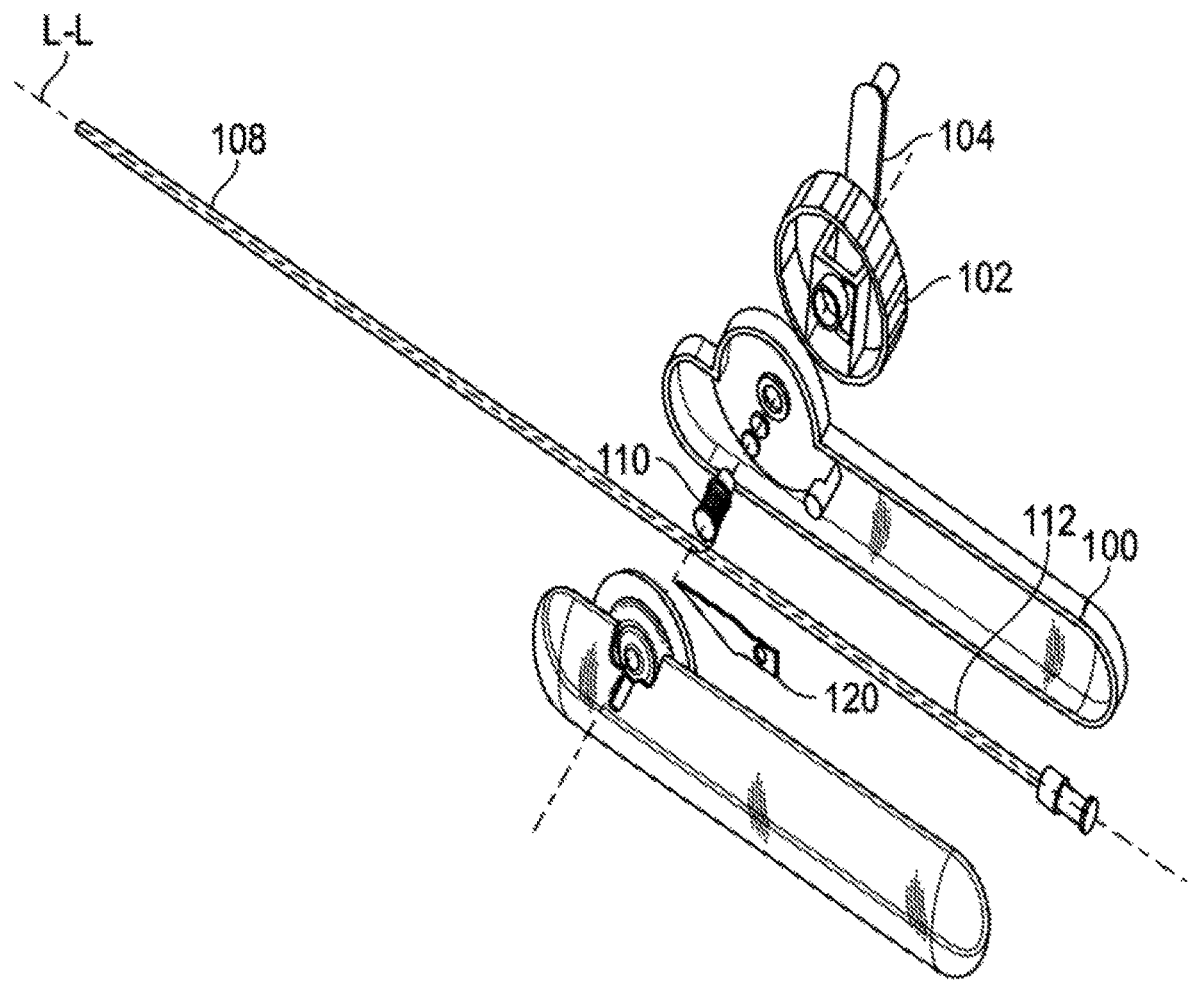
FIGS. 4A, 4B and 4C illustrate yet another embodiment of the handle in FIG. 1 with the principles of FIGS. 1-3.

Referring to FIG. 4A, the housing 100 extends along axis L-L from a first end (distal) to a second end (proximal). A sharp member 120 (in the form of a single blade) is disposed in the housing 100 and configured to cut the outer sheath 108 along an outer surface of the generally tubular outer sheath 108. After the blade 120 is a spool hub 110 mounted in the housing 100 and configured to wind the outer sheath 108 after being cut by the sharp member 120.

Figure 2A:
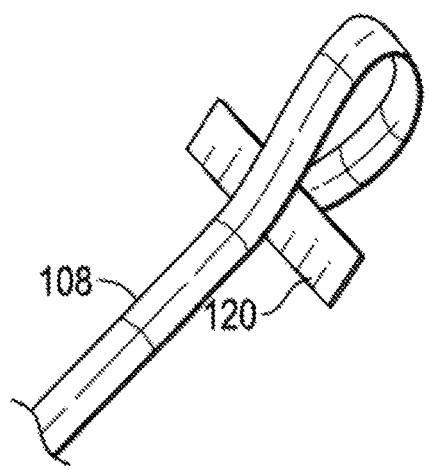
FIGS. 2A, 2B, and 2C illustrate the internal operation of the handle in FIG. 1.
Figure 2B:
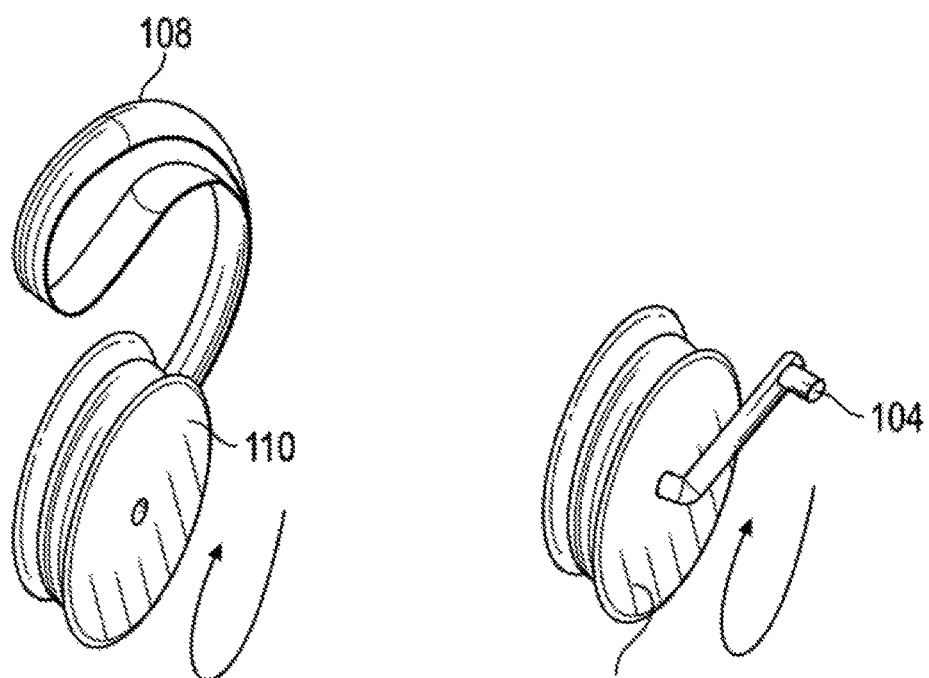

To explain the need for a blade or a similar cutting implement, such as sharp member 120, reference is made to FIGS. 2A and 2B. In FIG. 2A, it can be seen that in order to wind tubular sheath 108 in a more compact configuration, it is advisable to substantially flatten the tubular shape by cutting through at least one outer surface of the tubular member (and alternatively both surfaces as shown here in FIG. 2A). This allows for a more efficient technique to wind the outer sheath onto hub 110 using the thumbwheel 102 in the first mode of actuation or using the crank arm 104 in the second mode of actuation as indicated in FIG. 2C.

Figure 2C:
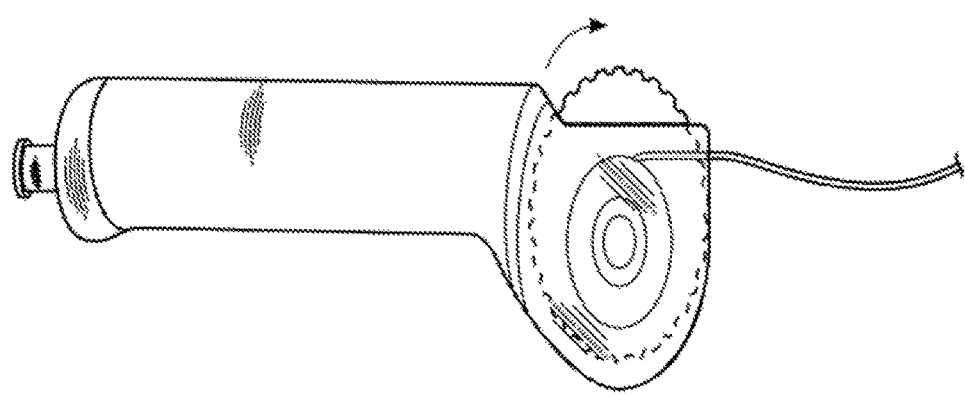
Figure 3A:
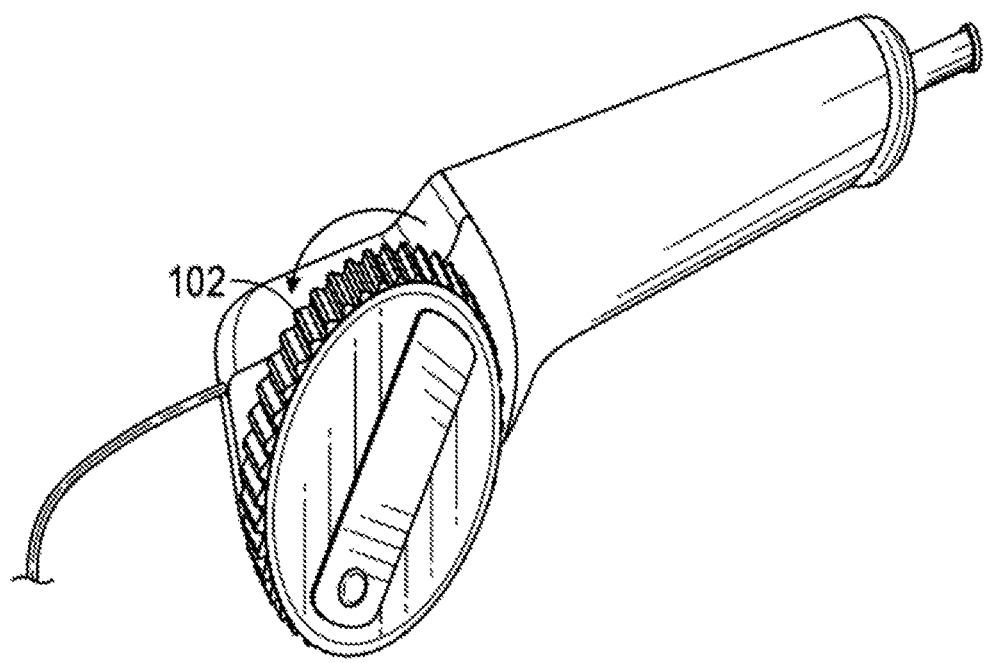
FIGS. 3A and 3B illustrates the external operation of the handle in FIG. 1.
Figure 3B:
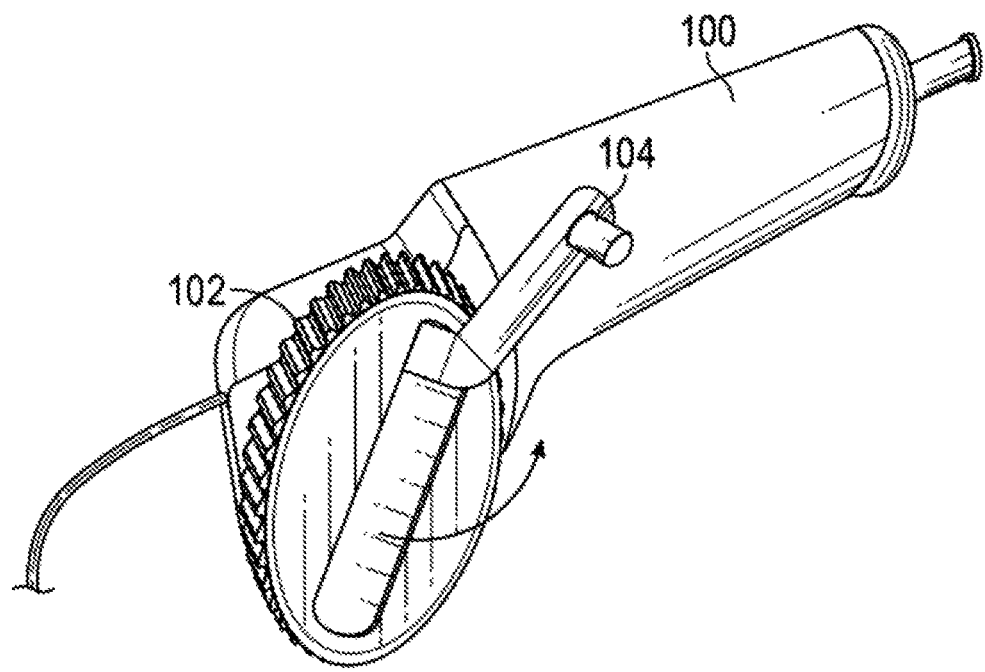

FIGS. 3A and 3B illustrate the external operation of the handle 100 to allow for the internal operation in FIGS. 2A-2C. A wheel 102 is mounted on the housing 100 and coupled (directly or via a gear train for even finer rotation) to the hub 110 such that rotation of the wheel 102 causes the outer sheath 108 (at the distal end) to move along the longitudinal axis L-L relative to the inner shaft 80 toward the second end or proximal end. Direct manipulation of wheel 102 using the first mode of actuation ergonomically favors translating outer sheath 108 at the first rate of change of distance (i.e., first speed) as may be imparted by the physician manipulating the wheel 102 with a thumb. To increase the winding speed, the second mode of actuation involves reconfiguring wheel 102 by flipping the crank arm 104 can be flipped out from its slot 105 of the wheel 102 so that rotation of the crank arm 104 causes the outer sheath 108 to move along the longitudinal axis L-L relative to the inner shaft 80 toward the second end (proximal end). Manipulation of the crank arm 104 using the second mode of actuation ergonomically favors translating outer sheath 108 at the second rate of change of distance (i.e., second speed), which is faster than the first rate of change to complete release of the stent more quickly. This is due to the greater relative ease of turning wheel 102 by crank arm 104 as compared to pushing wheel 102 with the physician's thumb, representing an ergonomic efficiency. Notably, from a context of human dynamics, it is relatively easier to rotate crank arm 104 to achieve the second speed and retract outer sheath 108 at a greater rate and it is relatively easier to exert fine control over retractation of outer sheath 108 by manipulating wheel 102 with a thumb or similar appendage at the first speed.

In the preferred embodiments, the crank arm 104 is mounted to the wheel with a length of the crank arm being at least equal to the radius of the wheel and more preferably at least equal to the diameter D of the wheel 102. As noted earlier, the crank arm 104 is mounted on a pivot (not shown) proximate the circumference of the wheel 102 so that the crank arm 104 can be folded into the slot 105 formed out of the surface of the wheel. This provides for a substantially continuous surface (FIG. 1) so that the crank arm does not interfere with other components in its packaging.

Figure 4B:
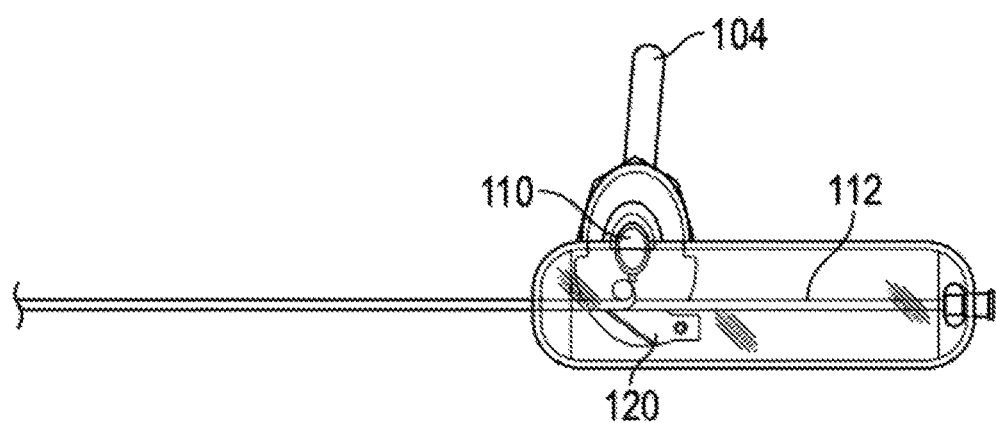
Figure 4C:
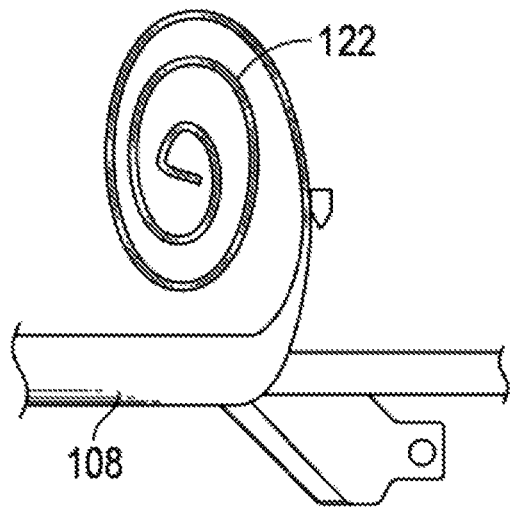

To ensure the ability to deliver saline or flush the device, a tubular member 112 is coupled to the outer sheath 108 at a location distal to the sharp member 120 as indicated in FIG. 4. Because blade 120 is proximal with respect to the tubular member 112, there is no separation and virtually no leakage through this coupling. In the preferred embodiment, a metal hypotube is utilized. Alternatively, a suitable polymeric tube can be utilized to achieve the same function.

To assist the operator in winding the outer sheath 108, a spiral spring 122 may be mounted in the housing with one end of the spiral spring 122 connected to the wheel 102 and the other end of the spiral spring 122 is connected to the housing 100 or the outer sheath 108.

As can be seen in FIG. 4B, the crank arm 104 has a length of about the same as diameter D of the wheel. In one embodiment, the wheel 102 is mounted offset with respect to the longitudinal axis L-L. Alternatively, the wheel 102 can be mounted with its axis aligned with respect to the longitudinal axis L-L. To present an aesthetic appearance, the wheel 102 can be mounted flush with respect to a side surface of the housing, shown here in FIGS. 1, 6E and 6F.

Figure 5:
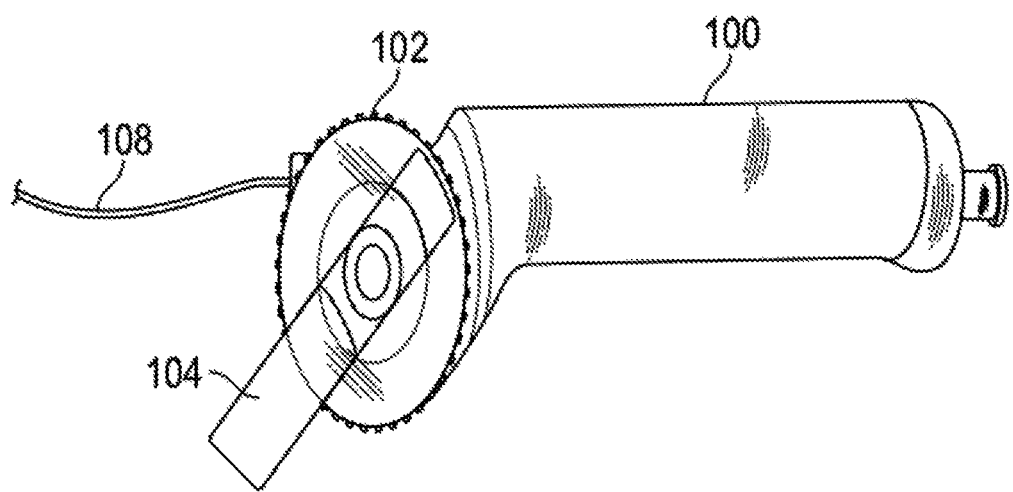
FIG. 5 is a schematic depiction according to an embodiment.

FIG. 5 shows an exemplary embodiment of the components discussed in FIGS. 1-4 earlier. Other design permutations of the handle 100 can be seen in FIGS. 6A-6H with different ergonomic design and placement of the wheel and crank arm. The designs in FIGS. 6A-6H can utilize the components illustrated and described in relation to FIGS. 1-5.

In operation, the distal end of the medical device delivery system 10 is preferably directed into a patient via a body passageway 300 of the patient. The medical device delivery system 10 may preferably follow along a guidewire (not shown) or travel through a previously placed guiding catheter (not shown), until the distal tip 90 is at a desired location in the body vessel 300 for treatment. As shown in FIG. 7A the distal tip 90 has preferably crossed the site of a lesion or stenosis 302. When the device is properly in an initial position (FIG. 7A), the physician releases or breaks off the lock of the handle (not shown for brevity and not required in all embodiments). The lock may be releasable only once, or may be capable of repeatedly being engaged and released. Such a locking mechanism preferably resists inadvertent or accidental movement or retraction of the stent delivery system components during packaging, sterilization, shipping, storage, handling and preparation.

After the lock is released, the wheel 102 can be rotated slowly such that the outer sheath 108 is retracted towards the operator by employing the first mode of actuation. In this configuration, there is one to one feedback between motion of wheel 102 and retraction of outer sheath 108 that may be exploited by the physician to control the rate at which stent 200 or other medical device is initially deployed. In particular, the use of the wheel 102 coupled to the outer sheath 108 allows precise and sensitive adjustment to pull the outer sheath 108 back slightly. This small movement exposes a small portion of the medical device, in this case a stent 200, as shown in FIG. 7A. In this configuration, the handle 100 will hold the outer sheath 108 in position relative to the inner wire 80, resisting further inadvertent expansion of the stent 200. The physician then has the time and flexibility of procedure to selectively optimize and make any final adjustments to the position of the medical device and delivery system within the desired site, as illustrated in FIG. 7A. This precise adjustment of the position of the stent 200, before any portion of the stent 200 touches the body passage or vessel 300 in a manner that might inhibit further positional adjustment, is preferable.

Figure 6A:
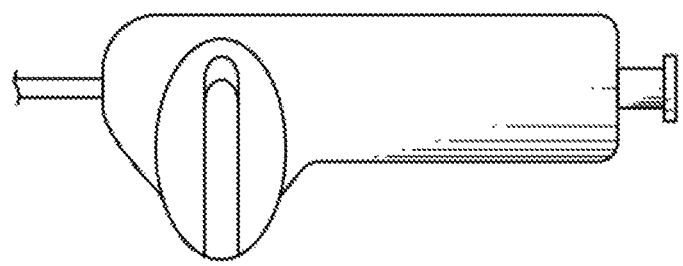
FIGS. 6A, 6B, 6C, 6D, 6E, 6F, 6G and 6H illustrate yet more permutations of the embodiment of FIG. 1.
Figure 6B:
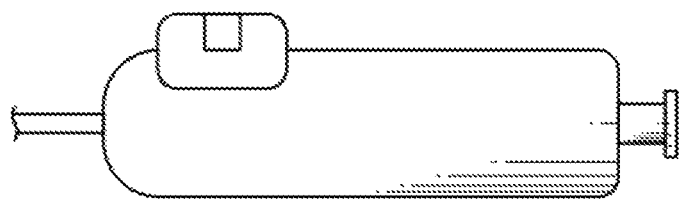
Figure 6C:
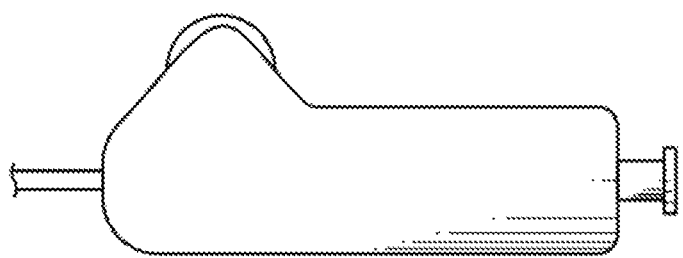
Figure 6D:
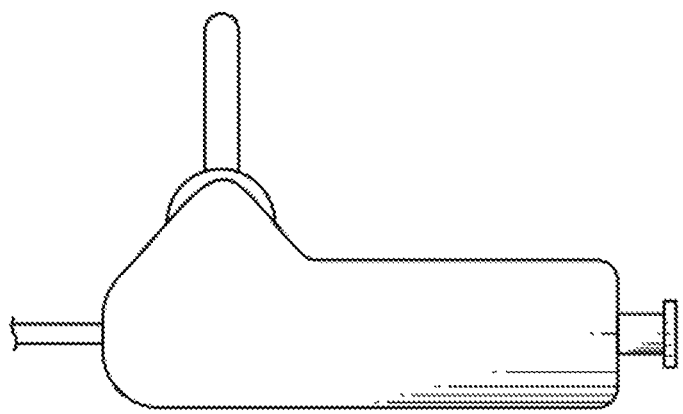
Figure 6E:
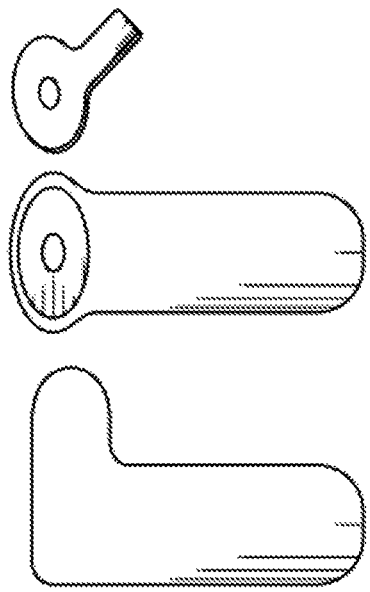
Figure 6F:
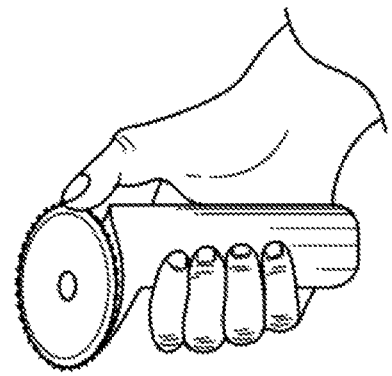
Figure 6G:
Figure 6H:
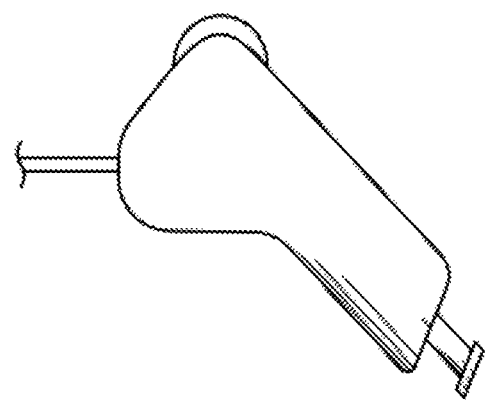

When the physician is satisfied with the positioning, as it appears on a fluoroscopic x-ray video screen for example, the physician may continue to rotate the wheel 102 to further withdraw the outer sheath 108 using the first mode of actuation, as shown in FIG. 6A, by primarily manipulating wheel 102 with a thumb or similar appendage.

Figure 7B:
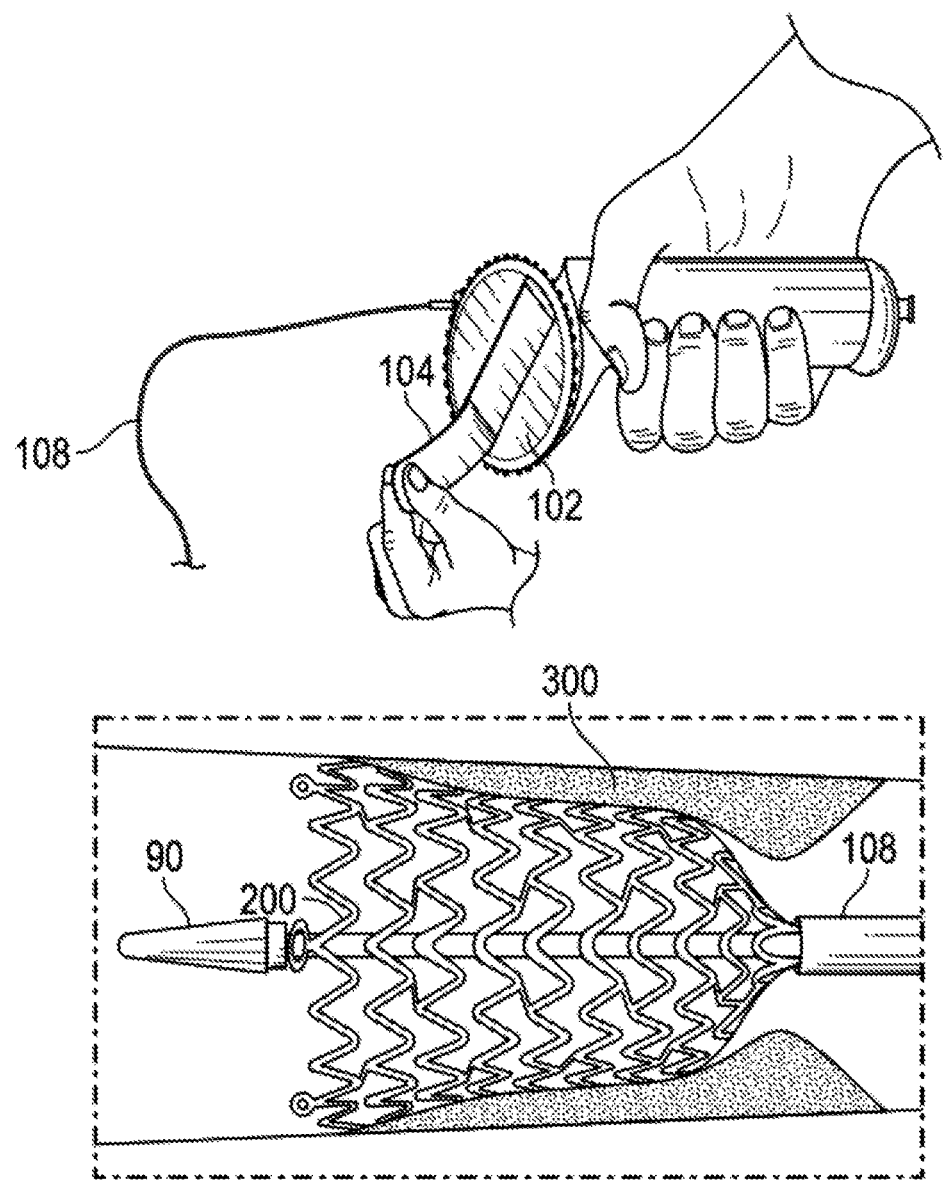

Upon initial contact of the stent 200 with the vessel wall, or when the stent is 200 expanded sufficiently to independently hold its position, or at any desired point, the physician may flip out crank arm 104 and crank the wheel with greater ergonomic efficiency using the second mode of actuation to achieve an increased retraction speed, as shown in FIG. 7B. This second mode of withdrawing the outer sheath 108 allows relatively large-scale and rapid movement, at whatever speed the physician wishes, to quickly deploy the medical device. Depending on the configuration, outer sheath 108 may be cut by sharp member 120 during either the second mode of actuation or during a combination of the first mode of actuation and the second mode of actuation.

Various materials may be selected for the components of the present invention, including any material having the desirable performance characteristics. In the particular embodiment shown in the drawings, the inner and outer shaft members and, strain relief and distal tip may be made of any biocompatible and suitably flexible yet sufficiently strong material, including polymers of various types. Possible selections for such materials include nylons or polyamides, polyimides, polyethylenes, polyurethanes, polyethers, polyesters, etc. In the alternative, some portion or all of the inner and/or outer shaft member may be formed of a flexible metal, including for example stainless steel or nitinol hypotube. The stent 200 is preferably made of any biocompatible material that is strong and rigid, including for example stainless steel, platinum, tungsten, etc. The components of the handle of the present invention are preferably made of a material that is strong and rigid, including for example inflexible polycarbonates, or even some metal components. In addition, the inner shaft member distal tip may preferably be provided with a through lumen adapted to receive a guidewire.

Of course, many different variations are included within the scope of the present invention. Some of these variations or alternative embodiments include any possible arrangement of sizes, materials, and designs within the scope of the claims.

By virtue of the disclosure provided herein, a method of delivering a self-expanding stent to selected location in a body vessel can be utilized. The method can be achieved by: moving a stent 200 to a selected location in a body vessel 300, the stent 200 being disposed adjacent a catheter tip 90 and confined between an inner shaft 80 and an outer sheath 108 at a distal end of a delivery system 10; winding the outer sheath 108 so that the outer sheath is moved relative to the inner shaft 80 along a direction from the distal end toward a proximal end of the delivery system 10 using a first mode of actuation that ergonomically favors translation of the outer shaft at a first rate to allow a portion of the self-expanding stent 200 to be expanded into the body vessel 300; cutting through at least an outer surface of the outer sheath so that the outer sheath 108 is substantially flattened; and rotating the substantially flattened outer sheath 108 using a second mode of actuation that ergonomically favors translation of the outer shaft 108 at a second rate that is greater than the first rate so that the outer sheath is moved relative to the inner shaft 80 along a direction from the distal end toward a proximal end of the delivery system 10 to allow substantially full expansion of the self-expanding stent 200 in the body vessel 300. The first mode of actuation involves manipulating wheel 102 directly to cause the outer sheath to move relative to the inner shaft, then reconfiguring wheel 102 and manipulating the reconfigured wheel using the second mode of actuation. In one embodiment, reconfiguring the wheel involves deploying a crank arm of the wheel. As desired, the substantially flattened outer sheath is wound using the first mode of actuation before rotating the substantially flattened outer sheath using the second mode of actuation.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A stent delivery system comprising:
   a catheter tip coupled to an inner shaft and an outer sheath with a stent disposed between the inner shaft and the outer sheath, the inner shaft and the outer sheath extending from a distal end to a proximal end;
   a housing extending along a longitudinal axis from a first end to a second end;
   a sharp member disposed in the housing and configured to cut the outer sheath along a surface of the outer sheath;
   a spool hub mounted in the housing and configured to wind the outer sheath after being cut by the sharp member; and
   a wheel mounted on the housing and coaxially coupled to the spool hub such that rotation of the wheel causes the outer sheath to move along the longitudinal axis relative to the inner shaft toward the second end, wherein the wheel is configured for a first mode of actuation that ergonomically favors translation of the outer sheath at a first rate and for a second mode of actuation involving a reconfiguration of the wheel that ergonomically favors translation of the outer sheath at a second rate that is greater than the first rate.

2. The stent delivery system of claim 1, further comprising a crank arm mounted to the wheel so that continuous rotation of the crank arm causes the outer sheath to move along the longitudinal axis relative to the inner shaft toward the second end, wherein the first mode of actuation comprises manipulating the wheel directly and the second mode of actuation comprises manipulating the crank arm.

3. The stent delivery system of claim 2, in which the crank arm is mounted to the wheel with a length of the crank arm being at least equal to the radius of the wheel.

4. The stent delivery system of claim 2, in which the crank arm is mounted on a pivot proximate the circumference of the wheel so that the crank arm can be folded into a slot formed out of a surface of the wheel to present a substantially continuous surface.

5. The stent delivery system of claim 1, in which a tubular member is coupled to the outer sheath at a location distal to the sharp member.

6. The stent delivery system of claim 1, in which a hypotube is coupled to the outer sheath at a location distal to the sharp member.

7. The stent delivery system of claim 1, in which a spiral spring is mounted in the housing with one end of the spiral spring connected to the wheel and the other end of the spiral spring is connected to the housing or the outer sheath.

8. The stent delivery system of claim 1, in which the wheel is mounted substantially flush with respect to a side surface of the housing.

9. A stent delivery system comprising:
- a housing extending along a longitudinal axis from a first end to a second end;
- an outer sheath configured for movement along the longitudinal axis and for retaining a stent;
- a sharp member disposed in the housing and configured to separate the outer sheath along a surface of the outer sheath;
- a spool hub mounted in the housing and configured to wind the outer sheath after being cut by the sharp member; and
- a wheel mounted on the housing and coaxially coupled to the spool hub such that rotation of the wheel causes the outer sheath to move along the longitudinal axis relative to the housing toward the second end to release the stent, wherein the wheel is configured for a first mode of actuation that ergonomically favors translation of the outer sheath at a first rate and for a second mode of actuation involving a reconfiguration of the wheel that ergonomically favors translation of the outer sheath at a second rate that is greater than the first rate.

10. The stent delivery system of claim 9, further comprising a crank arm mounted to the wheel so that continuous rotation of the crank arm causes the outer sheath to move along the longitudinal axis relative to the housing toward the second end, wherein the first mode of actuation comprises manipulating the wheel directly and the second mode of actuation comprises manipulating the crank arm.

11. The stent delivery system of claim 10, in which the crank arm is mounted to the wheel with a length of the crank arm being at least equal to the radius of the wheel.

12. The stent delivery system of claim 10, in which the crank arm is mounted on a pivot proximate the circumference of the wheel so that the crank arm can be folded into a slot formed out of a surface of the wheel to present a substantially continuous surface.

13. The stent delivery system of claim 9, in which a tubular member is coupled to the outer sheath at a location distal to the sharp member.

14. The stent delivery system of claim 9, in which a hypotube is coupled to the outer sheath at a location distal to the sharp member.

15. The stent delivery system of claim 9, in which a spiral spring is mounted in the housing with one end of the spiral spring connected to the wheel and the other end of the spiral spring is connected to the housing or the outer sheath.

16. The stent delivery system of claim 9, in which the wheel is mounted substantially flush with respect to a side surface of the housing.

* * * * *